(12) United States Patent
Ollett et al.

(10) Patent No.: US 6,880,954 B2
(45) Date of Patent: Apr. 19, 2005

(54) HIGH INTENSITY PHOTOCURING SYSTEM

(75) Inventors: Scott H. Ollett, Wake Forest, NC (US); Ross W. Lampe, Jr., Raleigh, NC (US)

(73) Assignee: SMD Software, Inc., Raleigh, NC (US)

( * ) Notice: Subject to any disclaimer, the term of this patent is extended or adjusted under 35 U.S.C. 154(b) by 232 days.

(21) Appl. No.: 10/290,736

(22) Filed: Nov. 8, 2002

(65) Prior Publication Data

US 2004/0090794 A1 May 13, 2004

(51) Int. Cl.$^7$ .............................................. F21V 5/00
(52) U.S. Cl. ...................... 362/245; 362/294; 362/373; 362/555; 362/580; 362/800; 433/29
(58) Field of Search .................................. 362/230, 245, 362/294, 373, 555, 580, 800; 433/29

(56) References Cited

U.S. PATENT DOCUMENTS

| | | | |
|---|---|---|---|
| 4,337,759 A | | 7/1982 | Popovich et al. |
| 5,404,869 A | | 4/1995 | Parkyn, Jr. et al. |
| 5,420,768 A | | 5/1995 | Kennedy |
| 5,490,048 A | * | 2/1996 | Brassier et al. ............. 362/238 |
| 5,634,711 A | | 6/1997 | Kennedy et al. |
| 5,690,417 A | | 11/1997 | Polidor et al. |
| 5,757,557 A | | 5/1998 | Medvedev et al. |
| 5,897,195 A | | 4/1999 | Choate |
| 6,102,696 A | | 8/2000 | Osterwalder et al. |
| 6,200,134 B1 | | 3/2001 | Kovac et al. |
| 6,331,111 B1 | | 12/2001 | Cao |
| 6,517,218 B1 | | 2/2003 | Hochstein |
| 6,547,423 B1 | | 4/2003 | Marshall et al. |
| 6,554,463 B1 | | 4/2003 | Hooker et al. |
| 6,638,063 B1 | * | 10/2003 | Otsuka ........................ 433/29 |
| 2001/0046652 A1 | | 11/2001 | Ostler et al. |
| 2002/0064043 A1 | | 5/2002 | Ariga et al. |

* cited by examiner

Primary Examiner—Stephen F Husar
(74) Attorney, Agent, or Firm—Coats & Bennett, P.L.L.C.

(57) ABSTRACT

A method and apparatus for curing photosensitive materials uses LEDs and an optical concentrator to generate high optical power intensities. An LED array, comprising a plurality of LED assemblies, generates collimated light. A collection lens functions as an optical concentrator and focuses the collimated light to a desired spot size at a desired location. The LED assemblies may be at least partially disposed in a cooling plenum, where the cooling plenum is at least partially defined by the collection lens. Each LED assembly within the LED array may be detachably coupled to a mounting surface, enabling easy replacement of individual LED assemblies within the LED array. The photocuring assembly may also include a redirecting assembly disposed between the collection lens and the desired location that may further concentrate the light at the desired location. The photocuring assembly may include more than one of the above features.

46 Claims, 6 Drawing Sheets

HIGH INTENSITY PHOTOCURING SYSTEM

BACKGROUND OF THE INVENTION

The present invention generally relates to a method and apparatus for curing photosensitive materials, and more particularly to a method and apparatus for intensifying and routing light, such as ultra-violet light, generated by light emitting diodes for the purpose of curing photosensitive materials.

One typical environment where photosensitive curing technology is encountered is in the curing of ultra-violet (UV) photosensitive materials during the manufacture of electronic components. The photocuring systems found in such environments typically use mercury-arc lamps to flood the UV sensitive material with UV light. While mercury-arc lamp technology is widely used, such technology has several disadvantages. The most obvious disadvantage is the life span of the mercury bulbs used in the mercury-arc lamps. Mercury bulbs have a relatively short life, typically 100–1000 hours. Further, the mercury bulb degrades non-linearly during its lifetime. As a result, conventional mercury-arc photocuring systems often require means to monitor and adjust the output power as the mercury bulb degrades. Further, mercury-arc lamps are typically powered on even during stand-by periods because they require cumbersome warm-up and cool-down cycles; as a result, much of the life of the mercury bulbs may be lost during these stand-by periods. Another disadvantage involves the broad spectrum of the light radiated by the mercury-arc lamp. A mercury-arc lamp radiates UV and infra-red (IR) light. Typically, UV band pass filters transmit the portion of the UV spectrum required for curing a particular photosensitive material. In addition, heat-rejecting IR filters are usually employed to prevent heating of the cure surface. Because the IR radiation creates a very hot lamp housing, transmission optics proximate to the lamp housing must be made of temperature resistant, UV-transmissive materials.

The introduction of UV light emitting diodes (LEDs) has created new alternatives for curing some UV sensitive materials. LED technology offers several advantages over the traditional mercury-arc technology. First, typical LEDs last between 50,000 to 100,000 hours, providing a significant lifespan improvement over mercury-arc technologies. Second, UV LEDs do not emit significant IR radiation, so heat-rejecting IR filtration is not required. As an added benefit, the reduced heat generation allows the use of economical UV transmitting polymers for lenses.

LED sources can also be turned on and off as required because LEDs do not require the warm-up and cool-down periods common in mercury-arc lamp systems. Some LED curing systems may implement driver circuits to control the current supplied to the LEDs. These circuits typically use a closed-loop system to monitor and control the output power of the LEDs, by controlling the drive current, to provide a stable and reliable UV source. These circuits may also define different curing cycles for different photosensitive materials, such as emitting a specific output power for a specific length of time.

Unfortunately, conventional LED sources and LED systems have relatively low output power compared to traditional mercury-arc lamps. While the lower output power LED photocuring systems have proven to be sufficient for some dental applications, many commercial and industrial UV sensitive materials require higher output powers, such as 0.5 to 3 $J/cm^2$, to cure properly. For example, some UV sensitive materials require between 100 to 600 $mW/cm^2$ of optical intensity to initiate and complete a five second cure. Historically, these intensities have not been achieved with LED-based curing systems.

U.S. Patent Application Publication 2001/0046652 to Ostler, et al., entitled "Light Emitting Diode Light Source for Curing Dental Composites," describes use of UV LEDs for curing of dental composites. The Ostler device increases the output intensity of UV light generated by an array of relatively low-power LEDs by concentrating collimated light generated by the array to a desired spot size at a desired location. While the Ostler system increases the output intensity of a UV curing system, the Ostler approach has several disadvantages. First, the Ostler LED array comprises a fixed array of LED chips and therefore does not allow replacement of individual LED units within the array. As a result, new entire units must be purchased to change the wavelength of the emitted optical power, or to replace one or more damaged or defective LEDs. Second, the Ostler cooling system is both complicated and likely insufficient for cooling the higher power UV LEDs now available on the market. Lastly, the Ostler publication does not discuss any methods or apparatus for capturing and redirecting any stray UV light to further intensify the output light at the desired location.

Therefore, there remains a need for high intensity LED-based curing systems that addresses one or more problems outlined above.

SUMMARY OF THE INVENTION

The present invention is directed to a method and apparatus for curing photosensitive materials. A photocuring assembly uses LEDs and an optical concentrator to generate high optical power intensities. An LED array, comprising one or more LED assemblies, generates collimated light. An optical concentrator, e.g., a collection lens, focuses the collimated light to a desired spot size at a desired location.

In one embodiment, the photocuring assembly includes a cooling plenum at least partially defined by the collection lens. The LED array of the photocuring assembly is at least partially disposed in the cooling plenum. Therefore, a cooling fluid, such as air, cools the LED array by flowing through the cooling plenum defined by the collection lens.

In another embodiment, each LED assembly comprises a base and an LED insert detachably coupled to the base. In yet another embodiment, the LED assemblies are detachably coupled to a mounting surface, such as a PCB. Both embodiments enable a user to modify the operating wavelength of the photocuring assembly by replacing one or more LED inserts or assemblies having a first operating wavelength with one or more LED inserts or assemblies having a second operating wavelength. In addition, damaged or defective LED inserts and/or assemblies may be replaced without necessitating the replacement of the entire LED array.

In another embodiment, the photocuring assembly includes a redirecting assembly disposed between the collection lens and the desired location. Due to the emission properties of conventional LEDs, the LED assembly may not collimate some minority of the light. As a result, the collection lens does not properly focus the non-collimated light exiting the LED array. The redirecting assembly uses refraction or optical reflection techniques to redirect at least a portion of any unfocused light to the desired location to increase the intensity at the desired location.

Other embodiments of the present invention may include photocuring assemblies that comprise one or more of the above embodiments. For example, the photocuring assembly may include the cooling plenum bounded by the collection lens and the detachably coupled LED assemblies.

DETAILED DESCRIPTION OF THE INVENTION

The present invention relates to a photocuring system that intensifies light emitted from one or more LEDs. The intensified light may be delivered to a remote location to induce a change in a photosensitive material 12 at the remote location, such as to cure the photosensitive material 12. Because one application for the present invention is curing UV curable materials, the discussions below use UV LEDs to illustrate the invention. However, it should be understood that the present invention is not limited to UV light or UV photocuring technologies.

Figure 1:
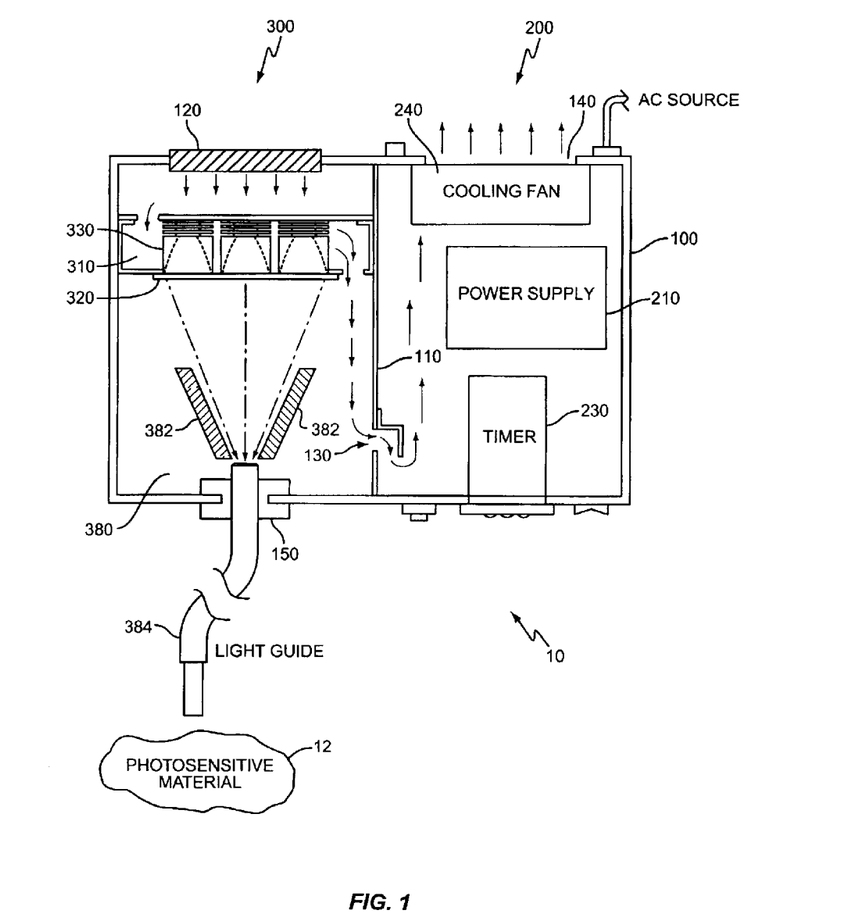
FIG. 1 illustrates a photocuring apparatus according to the present invention.

An exemplary photocuring system according to the present invention, generally indicated at 10, is shown in FIGS. 1–8. The photocuring system 10 includes an electrical assembly 200 and an optical assembly 300, both enclosed in a suitable housing 100. In addition to providing the mechanical structure, the housing 100 also provides a safety feature by isolating any potentially hazardous optical energy from a user. As shown in FIG. 1, the housing 100 may advantageously include an internal wall 110 that functions as a light baffle to isolate the portion of housing containing the main components of the electrical assembly 200 from any stray optical energy generated in the optical assembly 300. It should be noted that while FIG. 1 shows a single common housing 100 for the electrical and optical assemblies 200, 300, these assemblies may be mounted in separate interconnected enclosures, if desired.

Figure 2:
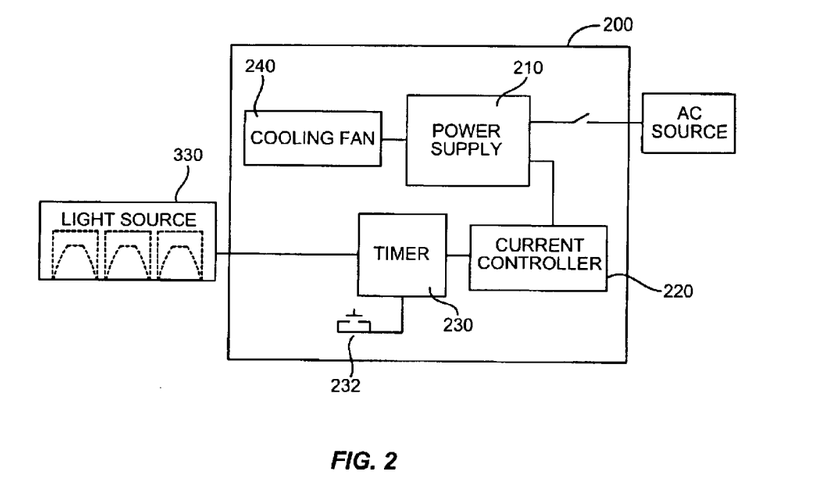
FIG. 2 illustrates electrical interconnections for the exemplary photocuring apparatus of FIG. 1.

The electrical assembly 200 supplies power to, and controls the operation of, the photocuring system 10. Referring to FIG. 2, the electrical assembly 200 may include a power supply 210, a current controller 220, a timer 230, and a cooling fan 240. The power supply 210 performs customary power supply functions, such as converting the incoming AC power to DC voltage and current, providing DC current to the current controller 220, providing DC power to the cooling fan 240, and the like. The current controller 220 adaptively controls the power delivered to an LED array 330 in the optical assembly 300 to enable the LED array 330 to generate stable, constant UV light. In addition, the current controller 220 may vary the power supplied to the LED array 330 to vary the optical power generated by the LED array 330 as desired. The timer 230 and optional cycle start switch 232 provide for further control of the operation of the LED array 330 to advantageously allow for triggered starts to the curing cycle, and optionally for adjustable time intervals for the curing cycles. The cooling fan 240 acts to pull cooling fluid, such as air, through the photocuring system 10 to avoid overheating the LED array 330. While discussed in greater detail below, the air is in general pulled into the housing intake 120, routed through the optical assembly 300, through the internal wall 110 to the electronic assembly 200, and then pushed out of the housing 100 by the cooling fan 240 via the housing exhaust 140.

The optical assembly 300 includes a collection lens 320, an LED array 330, a converging chamber 380, and a cooling plenum 310, as shown in FIG. 1. The LED array 330 generates high-power UV light. While an array of LEDs is used herein to illustrate the invention, it will be understood by those skilled in the art that the invention described herein applies equally well to a photocuring system using a single LED. As such, the term "LED array" as used herein is intended to mean one or more LEDs, such as a single LED or a plurality of LEDs arranged as desired. The collection lens 320 intensifies the light generated by the LED array 330 by focusing the light to a desired spot size at a desired location within the converging chamber 380. An optional redirection assembly 382 may be positioned in the converging chamber 380 to redirect light rays outside of the converging beam to the desired location to further intensify the light at the desired location, as discussed further below. The UV light intensified by the optical assembly 300 may then be delivered to the photosensitive material 12 at the remote location by coupling the intensified UV light into a light guide, such as an optical fiber 384, secured on one end to the housing 100 with a suitable fitting 150.

Figure 3:
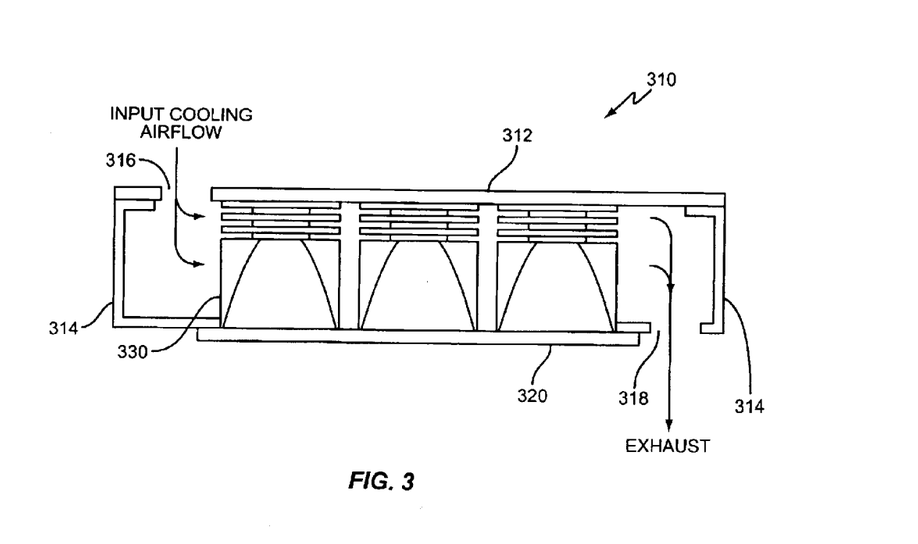
FIG. 3 illustrates an exemplary cooling plenum.

The LED array 330, which is discussed further below, is at least partially disposed in the cooling plenum 310, as shown in FIG. 3. For the FIG. 3 configuration, an electrical substrate 312, brackets 314, and the collection lens 320 bound the cooling plenum 310. Cooling air enters the cooling plenum 310 via intake port 316 and flows along cooling plenum 310 past LED array 330. The collection lens 320 confines the airflow to the cooling plenum 310 and forces the airflow past the LED array 330. The airflow exits the cooling plenum 310 via the exhaust port 318.

Figure 4:
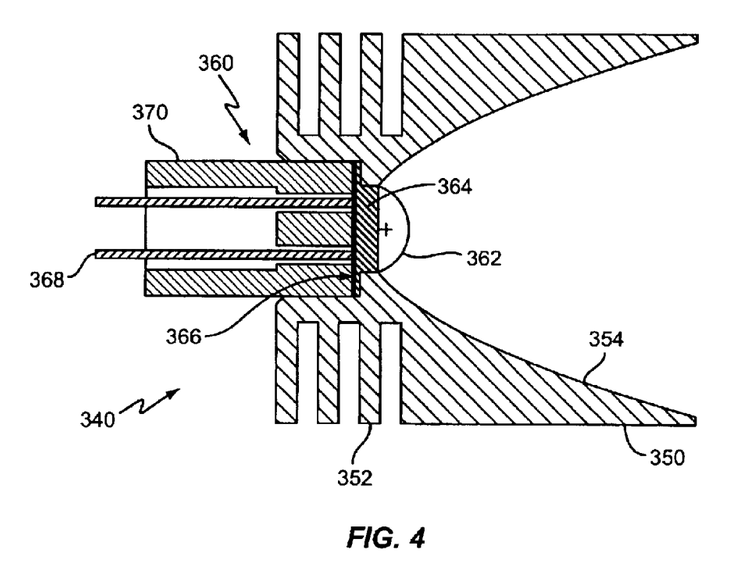
FIG. 4 illustrates an exemplary element of an LED assembly.

The LED array 330 comprises a plurality of LED assemblies 340. FIG. 4 illustrates an exemplary LED assembly 340 of the present invention. Each LED assembly 340 includes an LED insert 360 coupled to a collimator base 350. The collimator base 350 includes a heatsink 352 and a reflective cavity 354. The reflective cavity 354 may be shaped as a curve and functions to generally collimate and direct the diffuse LED light towards the collection lens. In a preferred embodiment, the reflective cavity 354 is shaped as a parabola. The reflective cavity 354 should be fabricated from a metal or metal alloy, e.g., an aluminum alloy, and should be highly polished to efficiently reflect the optical energy radiated at the LED's operational wavelength. In a preferred embodiment, the collimator base 350 is a single unit formed from a solid piece of material. Alternatively, the heatsink 352 and reflective cavity 354 are separately manufactured and joined together to form the collimator base 350.

The LED insert 360 includes an LED 362, LED base 364, thermal conductive adhesive 366, LED terminals 368, and a thermal post 370. An LED die (not shown) emits radiant energy at an operational wavelength preferably within the range of 315 nm to 450 nm. The LED die is typically positioned on a metalized ceramic standoff (not shown) that electrically isolates the LED die from the LED base 364, although this is not required. The standoff, or its equivalent, raises the LED die above the LED base 364 to maximize the light emitted by the LED 362 and collimated by the reflective cavity 354 of the collimator base 350. Wire bonds (not shown), insulated from the LED base 364, electrically connect the LED die to the LED terminals 368.

The LED 362 is fixedly attached to the LED base 364 and inserted into the thermal post 370 to form the LED insert 360. The LED base 364 is typically fabricated from steel or copper alloys, and plated with gold or silver. Alternatively, the LED base 364 may be fabricated from a ceramic material. Thermal conductive adhesive 366 secures the LED base 364 to the thermal post 370 and improves the thermal conduction from the LED 362 to the heatsink 352. The thermal post 370, preferably constructed of an aluminum alloy, includes holes to pass the LED terminals 368 formed along the longitudinal axis of the thermal post 370. Insulative sleeving, such as plastic, rubber, or fiber (not shown), placed over the LED terminals 368 electrically isolates the LED terminals 368 from the thermal post 370. Alternatively, a hard-anodized insulating coating added to the internal surface of the thermal post 370 electrically isolates the LED terminals 368 from the thermal post 370.

The assembled LED insert 360 is then inserted in the collimator base 350 to position the LED 362 at a desired location within the reflective cavity 354. Once the LED 362 is positioned at the desired location within the reflective cavity 354, the LED insert 360 is either fixedly or detachably coupled to the collimator base 350 by any means well known in the art. For example, the LED insert 360 may include threads (not shown) for threadably coupling the LED insert 360 to the collimator base 350, with locking compound optionally added to fix the LED insert 360 to the collimator base 350. Alternatively, adhesive may secure the LED insert 360 to the collimator base 350. The LED insert 360 coupled to the collimator base 350 forms the LED assembly 340.

In a preferred embodiment of the present invention, each LED assembly 340 is detachably coupled to an electrical substrate 312, such as a printed circuit board (PCB), to form the LED array 330 (FIG. 1). Sockets electrically connected to PCB 312 provide detachable electrical connection points for the LED terminals 368. Alternatively, a connector may be soldered to the LED terminals 368 for detachably connecting the LED assembly 340 to the PCB 312. Preferably, the electrical connection points also provide mechanical support for the LED assemblies 340. For example, the connections may be via known screw lamp base socket (with corresponding threads on the LED base 364) for a threaded coupling between the LED assemblies 340 and the PCB 312, or known bayonet or wedge type lamp base sockets may be used instead. Alternatively, separate mechanical means of connection, such as dedicated screws, clips, or the like, may be used to mechanically couple the LED assemblies 340 to the PCB 312. As another alternative, L-shaped LED terminals 368 may be used to extend through suitably configured slots in the PCB 312, with the LED assembly 340 rotated 90° to align the LED terminals 368 with contact pads on the PCB 312 and to seat the LED assembly 340 against the PCB 312 using the inherent spring force generated by slightly-deflecting the LED terminals 368 against the far side of the PCB 312. Any of these approaches may be used to detachably couple the LED assemblies 340 to the PCB 312. As should be clear from the above, it is preferred that the coupling be both mechanical and electrical, but some embodiments may merely electrically couple the LED assemblies 340 to the PCB 312, with the LED assemblies 340 being otherwise mechanically supported.

The number of LED assemblies 340 employed determines the size of the LED array 330 and the desired output intensity. For example, five LED assemblies 340 can generate approximately 500 mW/cm$^2$ of desired output intensity at a wavelength of 400 nm when inserted into an LED array 330 of a photocuring system 10 according to the present invention; forty LED assemblies 340 can generate at least 1,000 mW/cm$^2$ of desired output intensity at a wavelength of 400 nm, and preferably approximately 4,000 mW/cm$^2$.

The detachably coupled LED assemblies 340 and/or detachably coupled LED inserts 360 have several benefits. For example, a user can change the operating wavelength of the photocuring system 10 by replacing one or more LED assemblies 340 or one or more LED inserts 360 having a first operating wavelength, i.e., 315 nm, with one or more replacement LED assemblies 340 or LED inserts 360 having a second operating wavelength, i.e., 400 nm. In addition, a user can replace damaged or expired LED assemblies 340 or LED inserts 360 without replacing the entire LED array 330. Further, a user can easily increase or decrease the output intensity by adding/removing LED assemblies 340 or LED inserts 360 to/from the LED array 330.

Figure 5:
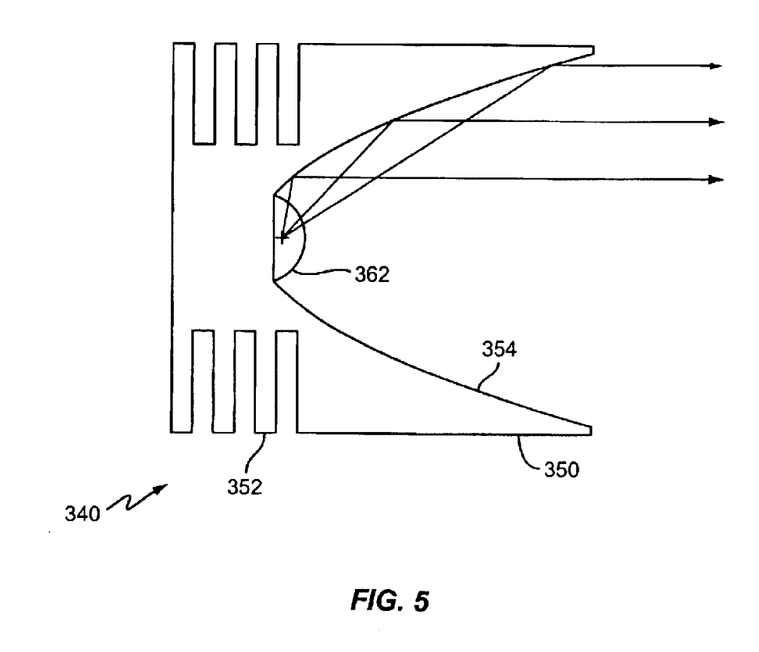
FIG. 5 illustrates an element of an LED assembly collimating LED light.

Regarding the optical properties of the optical assembly 300, each LED insert 360, including LED 362, emits diffuse light at a predetermined optical power and a predetermined optical wavelength. Exemplary LEDs 362 according to the present invention emit 150–250 mW of optical power at 315–450 nm. The reflective cavity 354 collimates a majority of the diffuse light emitted by the LED 362 when the LED 362 is placed at the desired location within the reflective cavity 354. A parabolic reflector 354 represents an exemplary reflective cavity 354 that collimates the majority of the light when the LED 362 is placed at or near the focal point of parabolic reflector 354, as shown in FIG. 5. It will be understood by those skilled in the art that the collimating means of the present invention is not limited to a parabolic reflector 354. Other LED collimating means well understood by those skilled in the art may also be implemented in the present invention.

The collection lens 320 intensifies the light generated by the LED array 330 by focusing the collimated light to a spot of a predetermined diameter at a predetermined location (FIG. 1). In a preferred embodiment, the LED array 330 uses a single collection lens or lens system for the entire LED array 330. Alternatively, the collection lens 320 may comprise an array of lenses, where each lens in the lens array corresponds to one or more LED assemblies 340 in the LED array 330. It will be appreciated by those skilled in the art that the collection lens 320 serves as a multifunction device in the present invention—in addition to intensifying the light generated by the LED array 330, the collection lens 320 also serves as a mechanical boundary of the cooling plenum 310, as discussed above.

Figure 6:
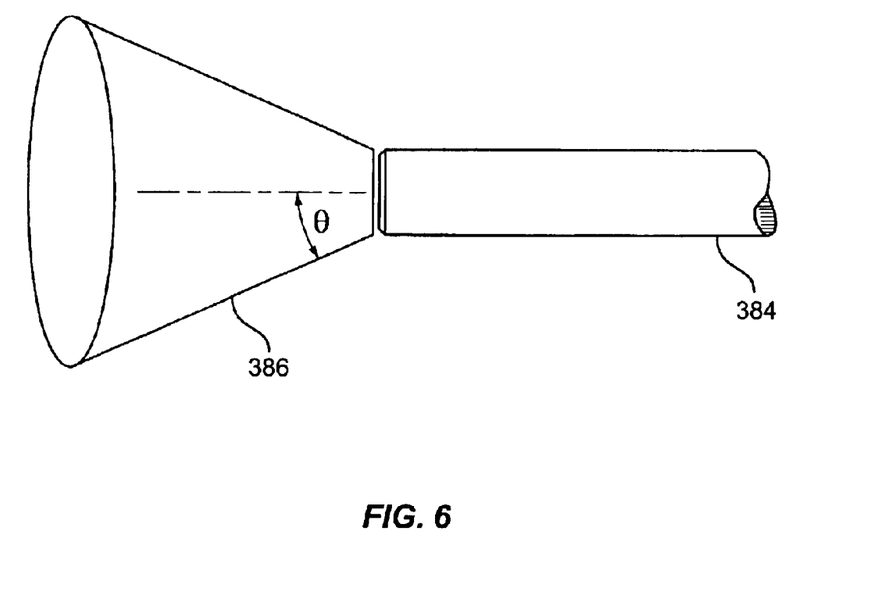
FIG. 6 illustrates a conventional light guide.

As mentioned previously, it is sometimes desirable to deliver the intensified UV light to a remote location via a conventional light guide, such as an optical fiber 384. The coupling properties of optical fibers 384 are well known in the art, and therefore, are only discussed briefly. As illustrated in FIG. 6, the coupling properties of optical fibers 384 are at least partially defined by an acceptance cone angle θ. Generally, only light entering the optical fiber 384 within the acceptance cone 386 couples to the optical fiber 384. Plastic, glass, and liquid-filled fibers typically exhibit acceptance cone angles θ ranging from 30° to 40°. Therefore, the convergence angle φ of the focusing light should be less than or equal to 30° to efficiently couple the light to the optical fiber 384. The convergence angle φ of the focusing light is inversely proportional to the focal length of the collection lens 320. Therefore, a lens designer should evaluate the properties of the selected collection lens or lens system 320 to ensure that the collection lens 320 will focus the light at the required convergence angle φ to the desired spot size. Designing a collection lens or a lens assembly 320 with a preferred convergence angle to focus collimated light to a preferred spot size is well understood in the art. Therefore, for simplicity, the details for designing such a collection lens or lens system 320 are not discussed further.

Figure 7:
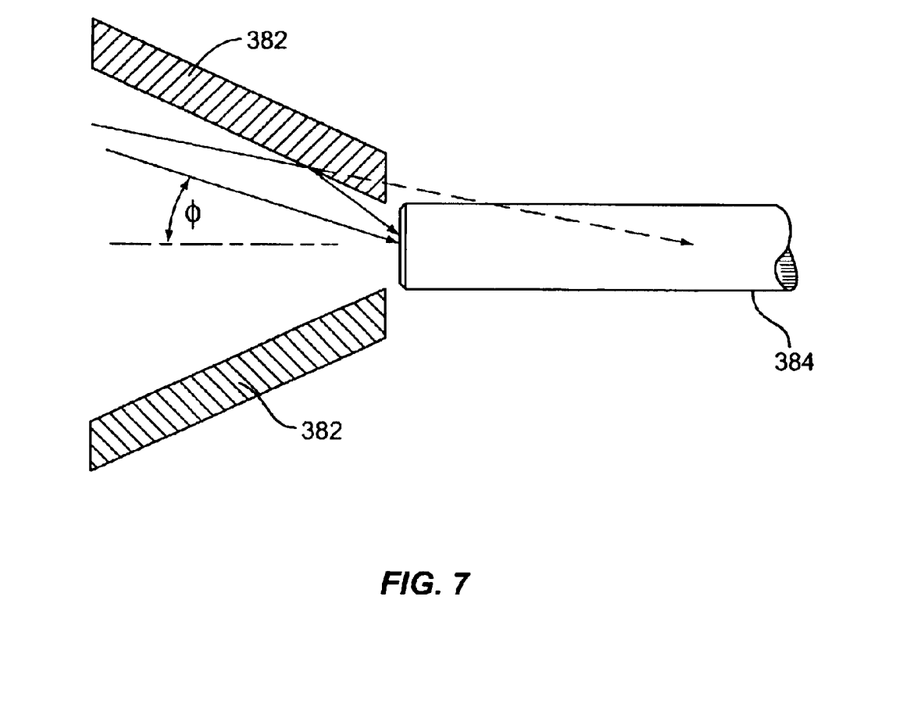
FIG. 7 illustrates an exemplary redirection assembly.

While a properly designed collection lens 320 will couple the majority of the collimated light to the fiber 384, a small minority of the light emitted by the LED array 330 is not collimated by the parabolic reflector 354, and therefore, is not properly focused by the collection lens 320. Most of this stray light converges either too quickly or too slowly to efficiently couple to the fiber 384. In addition, aberrations caused by the optical components may enlarge the focused spot. Therefore, to increase the intensity and/or to improve the fiber coupling efficiency, the present invention may optionally use a redirection assembly 382, as shown in FIG. 7, to redirect some of the stray light. The redirection assembly 382 can utilize refractive or reflective techniques to couple more radiant energy into the fiber 384. An exemplary redirection assembly 382 is a reflective cone that intercepts some of the outermost optical energy rays and redirects them towards the fiber 384. The additional light rays converging on the desired location increases the radiant intensity within the desired spot size and improves optical coupling to the fiber 384. A properly designed and positioned redirection assembly 382 can couple at least an additional 5% of the light into the fiber 384. One exemplary implementation can couple an additional 5–15% or more (preferably 10%) of the light into the fiber 384. As with other optical components of the present invention, the surface of a reflective redirection assembly 382 should be capable of reflecting radiant energy in the wavelength range of the emitted optical energy.

Figure 8:
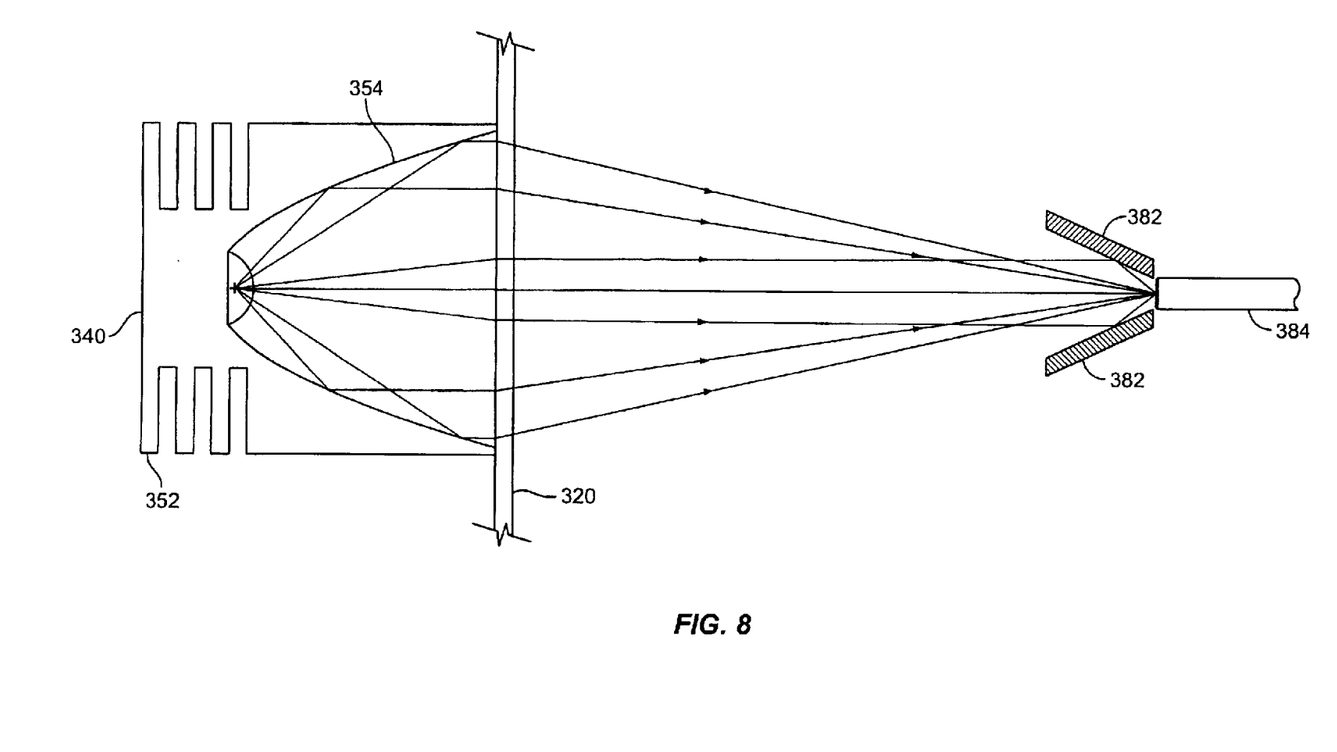
FIG. 8 illustrates exemplary light propagation according to the present invention.

To further exemplify the operation of the entire optical assembly, FIG. 8 illustrates an exemplary ray diagram for a single LED assembly 340, collection lens 320, redirection assembly 382, and optical fiber 384. It will be understood by those skilled in the art that a similar ray diagram results when the LED array 330 of a single LED assembly 340 is replaced by an LED array 330 of a plurality of LED assemblies 340. The parabolic reflector 354 of the LED assembly 340 collimates a majority of the diffuse light emitted by an LED 362 located at or near the focal point of the parabolic reflector 354. The collimated light entering the collection lens 320 focuses to a preferred spot size at the entrance to the fiber 384 and couples to the optical fiber 384. The non-collimated light entering the collection lens 320 also focuses at a location proximate the entrance to the optical fiber 384 and may or may not couple to the optical fiber 384. The optional redirection assembly 382 may redirect and couple a percentage of this stray light into the optical fiber 384.

Figure 9:
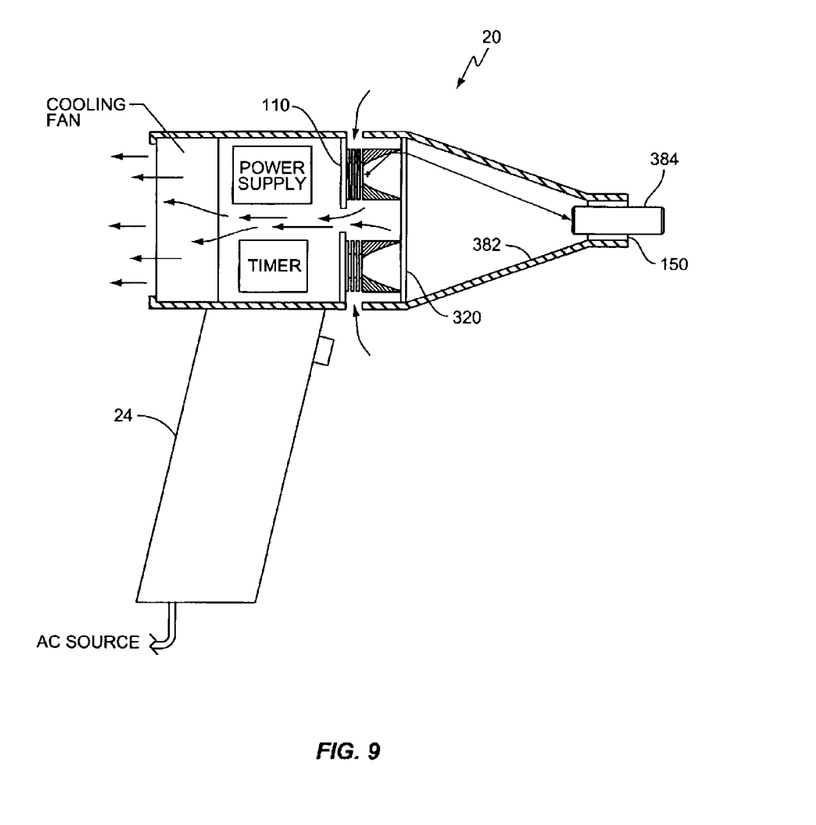
FIG. 9 illustrates an exemplary photocuring gun.

An alternate embodiment of the photocuring system 10 of the present invention is illustrated in FIG. 9 in the form of a hand-held photocuring tool 20. The photocuring tool 20 includes the electrical assembly 200 and optical assembly 300 in the head portion 22 of the photocuring tool 20. Intensified curing light is available at the exit of the fiber 384, located at one end of the head portion 22. A handle 24 enables a user to grip the photocuring tool 20 and direct the intensified curing light to a desired location. In this embodiment, the housing near the fiber 384 may be designed to act as the redirection assembly 382 for improving the coupling efficiency of the fiber 384 as described above.

As can be seen from the above, the various embodiments of the present invention include a cooling plenum 310 that is at least partially defined by the collection lens 320, readily replaceable LED assemblies 340 or LED inserts 360, and/or a redirection assembly 382 disposed between the collection lens 320 and the light guide 384, either alone or in combination. As a result, the present invention provides an alternative approach to generating intensified light using LEDs with significant advantages over the mercury-arc based approaches or the low-power approach of Ostler.

The foregoing description and drawings describe and illustrate the present invention in detail. However, the foregoing disclosure only describes some embodiments of a photocuring system. Accordingly, the present invention may be carried out in other specific ways than those set forth herein without departing from the essential characteristics of the invention. The present embodiments are, therefore, to be considered in all respects as illustrative and not restrictive, and all changes coming within the meaning and equivalency range of the appended claims are intended to be embraced therein.

What is claimed is:

1. A photocuring assembly, comprising:
    an LED array comprising a plurality of LED assemblies for generating collimated light;
    at least one collection lens optically downstream from said LED array; and
    a cooling plenum at least partially defined by said collection lens and having a cooling fluid flowing therein, wherein said LED array is disposed in said cooling plenum.

2. The photocuring assembly of claim 1 wherein each of said LED assemblies comprises a base and an LED insert and wherein at least one of said LED inserts is detachably coupled to said base.

3. The photocuring assembly of claim 1 wherein at least one of said LED assemblies is detachably coupled to a mounting surface.

4. The photocuring assembly of claim 3 wherein said mounting surface comprises an electrical substrate and wherein each of said LED assemblies is electrically coupled to said electrical substrate.

5. The photocuring assembly of claim 1 further comprising a fan to cause said cooling fluid to flow through said cooling plenum.

6. The photocuring assembly of claim 1 wherein said plurality of LED assemblies comprises a plurality of ultraviolet LEDs.

7. The photocuring assembly of claim 1 further comprising a light guide for collecting said light optically downstream from said collection lens.

8. The photocuring assembly of claim 7 further comprising a redirection assembly disposed between said collection lens and said light guide for reflectively redirecting at least a portion of said light to said light guide.

9. A photocuring assembly, comprising:
    an LED array comprising a plurality of LED assemblies, each of said LED assemblies comprising a base and an LED insert coupled to said base; wherein, for each of said LED assemblies, at least the LED insert is detachably coupled to a mounting surface; and
    at least one collection lens optically downstream from said LED array;
    a light guide for collecting light generated by said LED array optically downstream from said collection lens;
    a redirection assembly disposed between said collection lens and said light guide for redirecting at least a portion of said light to said light guide.

10. The photocuring assembly of claim 9 wherein said LED assembly comprises an ultra-violet LED.

11. A photocuring assembly, comprising:
an LED array comprising one or more LED assemblies for generating collimated light;
at least one collection lens optically downstream from said LED array to converge a majority of said light to within a predetermined area at a collection location distant from said collection lens; and
a redirecting assembly disposed between said collection lens and said collection location, said redirecting assembly redirecting at least a portion of said light other than said majority to fall within said area at said collection location.

12. The photocuring assembly of claim 11 wherein said redirecting assembly causes at least an additional 5% of said light to fall within said area at said collection location.

13. The photocuring assembly of claim 11 wherein said redirecting assembly causes at least an additional 10% of said light to fall within said area at said collection location.

14. The photocuring assembly of claim 11 wherein said redirecting assembly uses refraction to redirect said light other than said majority to said collection location.

15. The photocuring assembly of claim 11 wherein said redirecting assembly uses reflection to redirect said light other than said majority to said collection location.

16. The photocuring assembly of claim 15 wherein said redirecting assembly comprises a reflective conical area.

17. The photocuring assembly claim 11 further comprising a light guide for collecting said light at said collection location and delivering said light to a remote location.

18. The photocuring assembly of claim 17 wherein said light guide comprises at least one optical fiber and wherein said light guide collects said light within a predetermined collection angle.

19. A photocuring assembly, comprising:
an LED array comprising a plurality of LED assemblies for generating collimated light, each of said LED assemblies comprising a base and an LED insert coupled to said base; wherein, for each of said LED assemblies, at least the LED insert is detachably coupled to a mounting surface;
at least one collection lens optically downstream from said LED array to converge a majority of said light to within a predetermined area at a collection location distant from said collection lens; and
a cooling plenum at least partially defined by said collection lens and having a cooling fluid flowing therein, wherein said bases of said plurality of LED assemblies are disposed at least partially in said cooling plenum.

20. The photocuring assembly of claim 19 further comprising a redirecting assembly disposed between said collection lens and said collection location, said redirecting assembly redirecting at least a portion of said light other than said majority to fall within said area at said collection location.

21. The photocuring assembly of claim 19 wherein at least one of said LED inserts is detachably coupled to its respective base.

22. The photocuring assembly of claim 19 wherein at least one of said plurality of LED assemblies is detachably coupled to said mounting surface.

23. The photocuring assembly of claim 22 wherein at least one of said plurality of LED assemblies is threadably coupled to said mounting surface.

24. The photocuring assembly of claim 19 wherein each of said bases comprises a heatsink located on a first end of said base and a reflective collimating cavity located on a second end of said base opposite said first end, and further wherein said heatsinks are disposed in said cooling plenum.

25. The photocuring assembly of claim 19 further comprising a light guide for collecting said light at said collection location and delivering said light to a remote location.

26. The photocuring assembly of claim 19 wherein said mounting surface comprises an electrical substrate and wherein said plurality of LED assemblies are electrically coupled to said electrical substrate.

27. A method of operating a photocuring assembly, comprising:
providing an LED array comprising a plurality of LED assemblies, each of said LED assemblies including an LED insert coupled to a heatsink;
generating collimated light with said LED array;
intensifying said light with at least one collection lens optically downstream from said LED array; and
routing a flow of cooling fluid via a cooling plenum at least partially defined by said collection lens, wherein said heatsinks are disposed at least partially in said cooling plenum.

28. The method of claim 27 wherein routing said flow of cooling fluid comprises using a fan for routing said flow of cooling fluid through said cooling plenum.

29. A method of operating a photocuring assembly, comprising;
providing an LED array comprising a plurality of LED assemblies, each of said LED assemblies comprising a base and an LED insert coupled to said base, including a first LED assembly comprising a first base and a first LED insert;
detachably coupling said first LED assembly to a mounting surface; generating collimated light from said LED array using at least said first LED assembly;
thereafter, replacing at least one LED assembly in said LED array by decoupling at least said first LED insert from said mounting surface and detachably coupling a second LED insert to said mounting surface; and
generating collimated light from said LED array using at least said second LED assembly.

30. The method of claim 29 wherein replacing at least one LED assembly in said LED array comprises decoupling at least said first LED assembly, including its first LED insert, from said mounting surface and detachably coupling a second LED assembly to said mounting surface, said second LED assembly comprising a second base and said second LED insert.

31. The method of claim 29 detachably coupling comprises threadably coupling.

32. The method of claim 29 wherein generating collimated light from said LED array comprises generating collimated light at a first operating wavelength, wherein said first LED assembly emits light at said first operating wavelength.

33. The method of claim 32 wherein said first and second LED assemblies emit light at substantially equivalent operating wavelengths.

34. The method of claim 32 wherein said first and second LED assemblies emit light at different operating wavelengths.

35. A method of curing a photosensitive material at a curing location, comprising:
generating an intensified curing light, the steps comprising:

generating collimated light with an LED array comprising a plurality of LED assemblies;

generating said intensified curing light by converging a majority of said light to within a predetermined area at a predetermined location with at least one collection lens optically downstream from said LED array; and routing a flow of cooling fluid through a cooling plenum at least partially defined by said at least one collection lens, wherein said LED array is at least partially disposed in said cooling plenum; and delivering said intensified curing light to said curing location.

36. The method of claim 35 further comprising placing a photosensitive material at said curing location and exposing said photosensitive material with said intensified curing light.

37. The method of claim 36 wherein the step of delivering said curing light to said curing location comprises placing said photosensitive material at said predetermined location.

38. The method of claim 35 wherein the step of delivering said curing light to said curing location comprises collecting said intensified light at said predetermined location with a light guide and delivering said collected light through said light guide to said curing location.

39. The method of claim 38 wherein converging said majority of said light to within said predetermined area at said predetermined location further comprises placing a redirection assembly between said collection lens and said light guide and redirecting at least a portion of said light with said redirecting assembly to fall within said predetermined area at said predetermined location.

40. The method of claim 35 wherein said photosensitive material comprises material sensitive to light at a first wavelength and wherein generating said collimated light with said LED array comprises generating collimated light at said first wavelength with an LED array comprising at least one LED assembly that emits light at said first wavelength.

41. The method of claim 35 wherein at least one of said plurality of LED assemblies is detachably coupled in said LED array, and wherein generating said collimated light at said first wavelength comprises decoupling at least one LED assembly that emits light at a second wavelength and replacing said decoupled LED assembly that emits light at said second wavelength by detachably coupling an LED assembly to said LED array that emits light at said first wavelength.

42. The method of claim 41 wherein decoupling said at least one LED assembly comprises threadably decoupling said at least one LED assembly from said mounting surface.

43. The method of claim 41 wherein detachably coupling said second LED assembly comprises threadably coupling said second LED assembly to said mounting surface.

44. The method of claim 35 wherein each of said LED assemblies comprises a base and an LED insert detachably coupled to said base, and wherein generating said collimated light at said first wavelength comprises decoupling at least one LED insert that emits light at a second wavelength and replacing said decoupled LED insert by detachably coupling a different LED insert that emits light at said first wavelength.

45. The method of claim 44 wherein decoupling said at least one LED insert comprises threadably decoupling said at least one LED insert from said base.

46. The method of claim 44 wherein detachably coupling said second LED insert comprises threadably coupling said second LED insert to said base.

* * * * *